United States Patent [19]

Arnold

[11] Patent Number: 4,893,223
[45] Date of Patent: Jan. 9, 1990

[54] ILLUMINATION DEVICES FOR INSPECTION SYSTEMS

[75] Inventor: Aaron L. Arnold, Palm Beach Gardens, Fla.

[73] Assignee: Northern Telecom Limited, Montreal, Canada

[21] Appl. No.: 295,277

[22] Filed: Jan. 10, 1989

[51] Int. Cl.$^4$ ............................................. F21V 33/00
[52] U.S. Cl. ...................................... 362/252; 362/11; 362/33; 362/234; 362/800; 256/237
[58] Field of Search .................. 362/11, 33, 234, 240, 362/249, 250, 251, 252, 253, 800; 356/237

[56] References Cited

U.S. PATENT DOCUMENTS 4,688,939 8/1987 Ray ..................................... 356/237
4,814,667 3/1989 Tanaka ............................ 362/252 X Primary Examiner—Stephen F. Husar
Attorney, Agent, or Firm—Foley & Lardner, Schwartz, Jeffrey, Schwaab, Mack, Blumenthal & Evans

[57] ABSTRACT

Illumination devices for an inspection system which holds the article to be inspected in a particular location and having light emitting diodes disposed in a part spherical array to cause light to converge upon a restricted field of view in which the article is located. The device is of particular use for illuminating small articles which need to be inspected. The light emitting diodes are preferably operated selectively in groups to provide different light patterns upon the article under inspection.

12 Claims, 3 Drawing Sheets

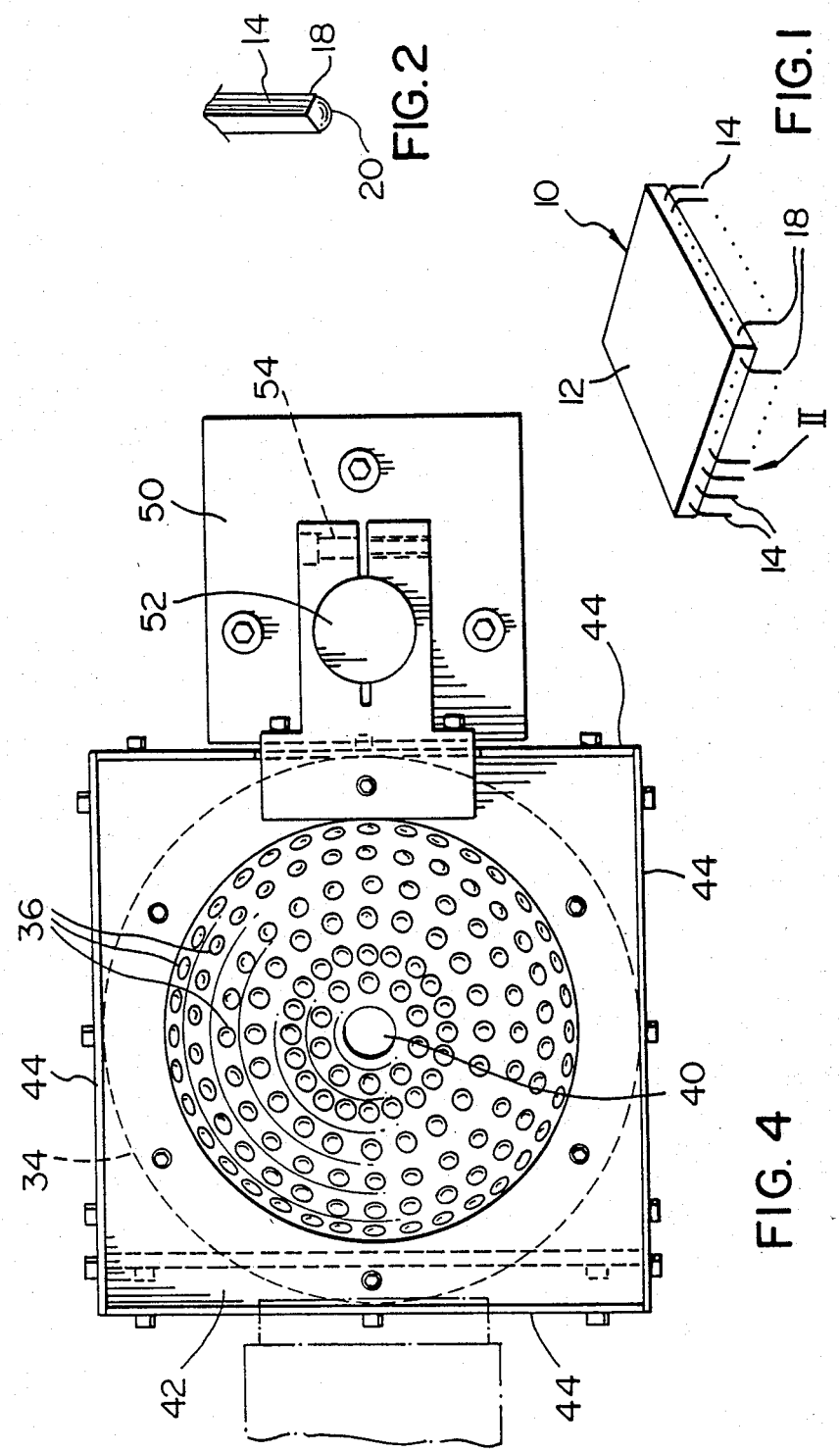

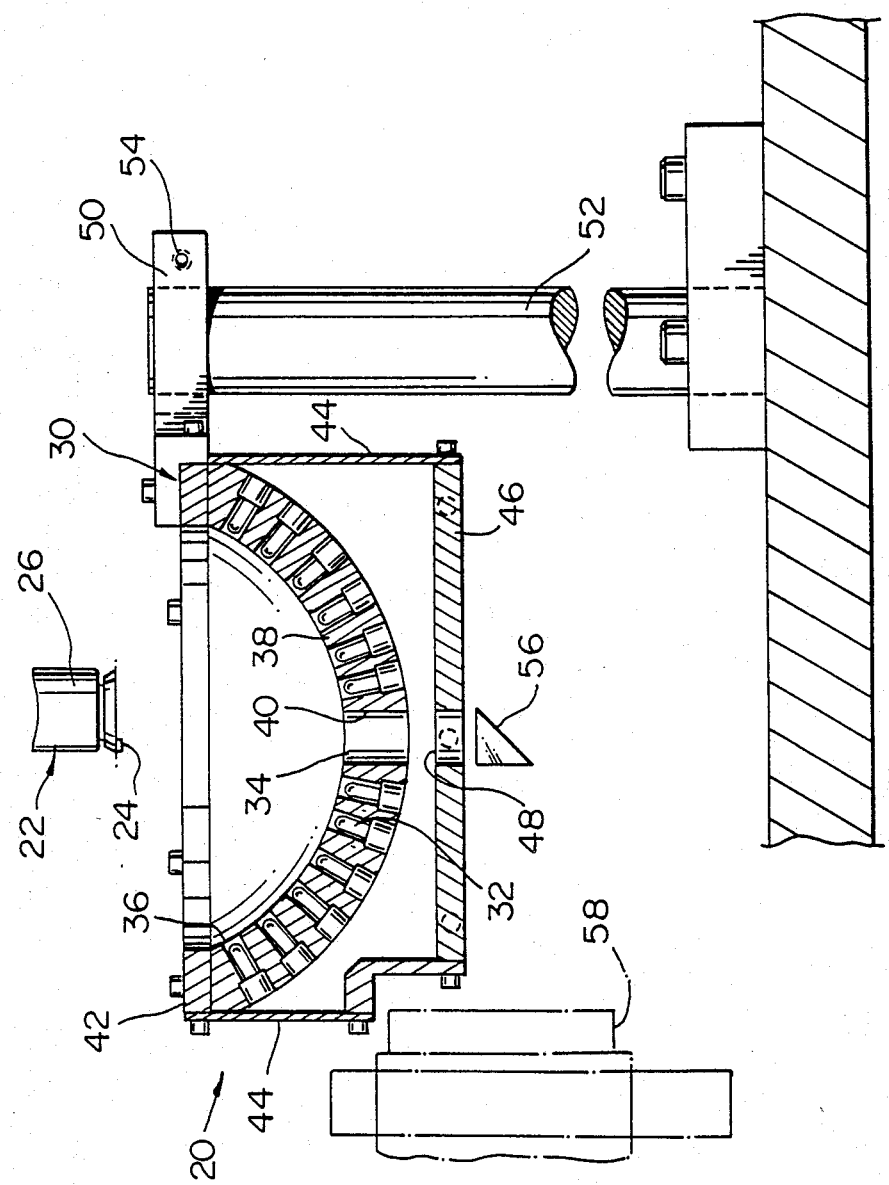

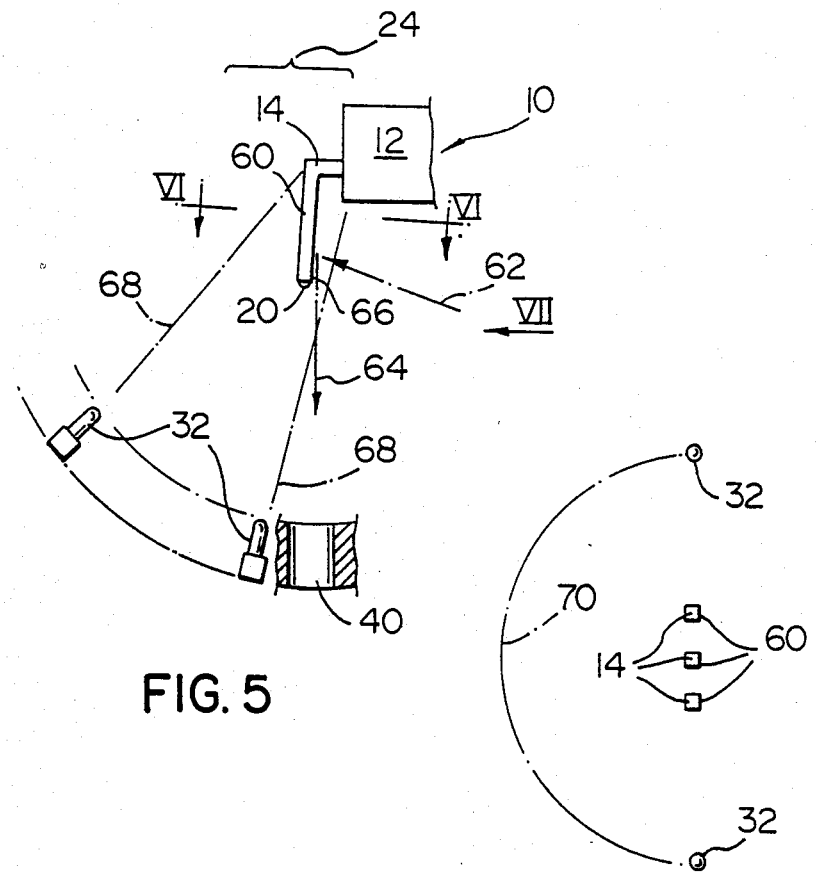
FIG. 5
FIG. 6
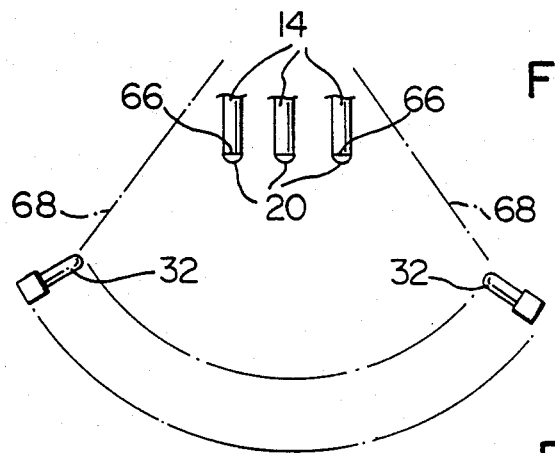
FIG. 7

ILLUMINATION DEVICES FOR INSPECTION SYSTEMS

This invention relates to illumination devices for inspection systems.

Illumination devices for inspection systems are of many types, each designed specifically for illuminating certain types and sizes of articles.

Some illumination devices are designed and used for illuminating small articles to enable the relative positions of the articles to be determined by inspection systems. Inspection systems are sometimes used for determining the relative positions of ends of terminal pins extending from bodies of surface mount components to be assembled onto circuit cards. Such circuit cards may be printed circuit boards or resistor networks. It is necessary for free ends of the terminal pins to be soldered onto terminal pads on circuit cards to secure the surface mount components thereon. As the terminal pads are precisely positioned on the circuit cards, it is also necessary for the free ends of the terminal pins to be precisely positioned relative to each other for faultless soldering to be provided. The free ends of the pins are normally precoated with solder to assist in the soldering operation. The solder coating creates a convex or hemispherical surface shape to the free ends of the pins.

However, in known illumination devices for inspection systems for determining the relative positions of the free ends of terminal pins, an annular light source is used for projecting light onto the free ends. The annular light source produces a cone of light which cannot be controlled. This cone of light is scattered and tends to illuminate side surfaces of the pins in addition to the surface under inspection. Reflected light from the pin side surfaces tends to be transmitted to the light sensitive recording means of an inspection system whereas light reflected from the convex end surface may be reflected away from the recording means. Thus, the position of the outline of the end of a pin may not be received by the recording means while reflected light from outside the outline further confuse the readings. In addition, the maintenance time for the known equipment is unacceptably high. For instance, the light source has an extremely limited life expectancy and it has been found in practice that an average life span is approximately twenty hours.

The present invention seeks to provide an illumination device which when used in an inspection system overcomes or minimizes the above problems.

An illumination device for an inspection system according to the present invention comprises a mounting means for mounting a plurality of spaced apart light emitting diodes in mounting locations disposed in a part spherical array to cause light from the diodes to converge upon a particular restricted field of view, and a location means for locating an article to be illuminated in the restricted field of view.

With the illumination device according to the invention, the mounting locations for the diodes are preferably connected into an electrical circuit so that when the light emitting diodes are mounted in those locations, they may be operable selectively in groups. Such groups may be located side-by-side angularly around the restricted field of view or alternatively, the groups may form annular groups centered upon an axis coincident with the restricted field of view. In a specific manner of performing the invention, the mounting means comprises a dish with a part spherical concave surface, the dish being formed with mounting apertures for holding the diodes within the wall of the dish. The apertures open at the concave surface of the dish to direct the light from the diodes towards the restricted field of view which is confronted by the concave surface. The groups of mounting locations may be sectorial groups of locations centered upon the restricted field of view, or alternatively, with the mounting apertures located on coaxial pitch circles centered on the restricted field of view, then the groups of locations may be arranged with the mounting positions of each group located upon a common pitch circle. With the mounting location connected in groups in the manner discussed above, the light emitting diodes may all be operated together to focus upon the restricted field of view or only a selected group or groups may be operated at any particular time. Where the groups are operated selectively, they will enable images to be provided of the same convex surface at the free end of a terminal pin from different positions so that light reflected to a light sensitive recording means clearly shows the position of the peripheral edge of the free end of the pin.

A further advantage of the illumination devices according to the invention is that when infrared light emitting diodes are used, this involves the use of an extremely small current, for instance one hundred and fifty milliamps for a group of in-series diodes totalling about fourteen diodes per group. When used in a pulse mode the current may be up to about six amps for each group. The devices according to the invention require little maintenance therefore and little or no "downtime" during operation.

One embodiment of the invention will now be described, by way of example, with reference to the accompanying drawings, in which:

FIG. 1 is an isometric view of a prior art surface mount component for a circuit card and which is to be inspected;

FIG. 2 is a view in the direction of arrow II in FIG. 1, and on a larger scale, showing the end of a terminal pin of the prior surface mount component;

FIG. 3 is a side elevational view, partly in section, of an inspection system incorporating an illumination device according to the embodiment and carrying a surface mount component;

FIG. 4 is a plan view of the system shown in FIG. 3;

FIG. 5 is a diagrammatic view, not to scale, showing a selection of groups of light emitting diodes of the illumination device for a preferred angular range of illumination of the free ends of a series of adjacent terminal pins of the surface mount component of FIG. 1;

FIG. 6 is a cross-sectional view of the pins taken along lines VI—VI in FIG. 5 and directed towards a mounting means of the device to further show the preferred range of illumination of FIG. 5; and FIG. 7 is a view in the direction of arrow VII in FIG. 5 still further to show the preferred range of illumination.

As shown in FIG. 1, a known surface mount component for mounting upon a circuit card for a printed circuit board comprises a body 12 of rectangular plan view, and a plurality of terminal pins 14 extending outwardly from side edges 16 of the body 12. Each of the terminal pins 14 extends outwardly from the side edges and then downwardly to terminate in a free end 18. As shown in FIG. 2, the end 18 of each pin is provided with a small globule of hardened solder, for the purpose of attaching the surface mount component to solder pads of a circuit card. The undersurface 20 of the globule has a general convexity in all directions so that it is substantially part spherical.

The inspection system shown in FIGS. 3 and 4 and according to the embodiment, is used for determining the relative positions of the free ends of the terminal pins so that the manufacturing accuracy of the component 10 may be judged together with its suitability for assembly onto a circuit card.

An illumination device of the inspection system, generally indicated at 20, comprises a location means 22 for holding the surface mount component 10 and for moving it incrementally into different positions of orientation in which free ends of successive series of the terminal pins 14 are located in a restricted field of view indicated at 24 in FIG. 3, to enable the relative positions of the free ends of each series to be determined. If successive series of pins overlap by, for instance, a single pin, then the relative positions of all the free ends may be determined. This method of determination of free end positions is known in the art of surface mount component manufacture and need not be discussed further. The location means 22 may be of any suitable design for holding the surface mount component in position and for controllably moving it in the manner desired. As shown in FIG. 3, the locating means comprises a vacuum operated gripping device 26 of known form for holding the body of such surface mount component 10. The gripping device is controllably movable by means not shown, in a rotational and horizontal fashion. Any known and suitable method for moving the device 26 in these directions with controlled accuracy may be used.

The illumination device also includes a mounting means 30 disposed beneath the location means 22. The mounting means is provided for mounting a plurality of spaced apart light emitting diodes 32 in mounting locations disposed in a part spherical array to cause light from the diodes to converge upon the restricted field of view 24. As shown in FIGS. 3 and 4, the mounting means 30 comprises a rigid dish 34 formed with mounting apertures 36 for the diodes 32. The apertures extend completely through the thickness of the dish and open at a part spherical concave surface 38 of the dish to direct the light from the diodes towards the restricted field of view 24 which faces the concave surface 38. The diodes are inserted into position within the apertures 36, as shown in FIG. 3, and are connected with an electrical circuit for the operation of the diodes. Electrical wiring of the circuit on the other side, the convex surface of the dish, is not shown for clarity. The radius of the part spherical inner surface 38 of the dish is approximately 2.12 inches. Thus, the diodes 32 are directed generally towards the center of radius while enabling the diodes to be effective in reflecting light from free end surfaces 18 located in the restricted field of view.

The diodes are infrared diodes for the purpose of providing sufficient power for inspection purposes. Alternatively, the infrared diodes may be replaced with red light emitting diodes. The infrared light emitting diodes provide a close match between the wavelength of the light source and the wavelength sensitivity of a silicon device camera which will be described below and which is to be used as a light sensitive recording means.

While the light emitting diodes 32 have been described as being received within mounting apertures of the dish 32, this structure is not essential. Alternatively, the diodes may be supported by a mounting framework without the use of a dish, bearing in mind that the important aspect is that the diodes are directed to cause convergence of their light towards the restricted field of view.

As shown in FIGS. 3 and 4, a hole 40 is symmetrically formed through the center of the dish for passage of reflected light from surfaces of any series of free ends 18 located in the restricted field of view 24. The mounting apertures are disposed on pitch circles having centers coincident with the center of the hole 40 which is substantially axially aligned with the general center of the restricted field of view.

The electrical circuit has terminals at groups of mounting locations for the diodes 32, these groups either being arranged sectorially around the center of the hole 40 or with each group of mounting locations located upon a common pitch circle. The number of groups is a question of choice and is also dependent upon dish design and numbers of diodes used. For instance, the mounting locations may be arranged in six, eight or ten sectors around the center of the hole 40. Alternatively, each group may comprise the mounting locations on each of the pitch circles shown in FIG. 4 whereby there are six groups. Otherwise, one or more groups may include mounting locations in one, two or more of the pitch circles. In this particular embodiment, there are one hundred and forty diode mounting locations with ten sectorial groups of fourteen mounting locations to each group. The fourteen diodes to each group are electrically connected in-series to operate with a current of one hundred and fifty milliamps. This may increase up to six amps in a pulsed mode.

With the diodes 32 in their locations, the circuitry is such that the groups of diodes may all be operated together or a group or selected groups of diodes may be operated selectively. With this type of selection being available with the illumination device, then different images of the same surface illuminated from different directions or combinations of different directions may result. The groups may also be chosen to prevent light reflection through the hole 40 from surfaces other than the free ends 18 of the pins. It follows that control may be exerted on the type of imagery which is produced by the reflected light from a surface under consideration.

As shown in FIGS. 3 and 4, the dish 34 is secured to and lies beneath a horizontal support 42 of square plan with a circular hole of sufficient size to permit the diodes to illuminate undersurfaces 20 of the pins 14 in the restricted field of view 24. From the support 42 depend four downwardly extending walls 44 which surround the dish 34. A bottom horizontal wall 46 lies beneath the dish so as to substantially totally enclose the convex surface of the dish except for a central hole 48 which lies in alignment with the hole 40. The whole of the dish and support assembly is secured to a support clamp 50 which is movable vertically upon a cylindrical shaft 52 and may be clamped in any desirable vertical position by a clamping screw 54 passing through bifurcated ends of the clamp to grip onto the cylindrical shaft.

Disposed beneath the lower wall 46 is a prism 56 of the inspection system, the prism 56 being in alignment through the two holes 40 and 48 with the restricted field of view 24 so as to receive light reflected from the under-surface 20 of any free end 18 in that position. The prism directs the reflected light to light sensitive recording means which, in this embodiment, comprises a silicon device camera 58 referred to above. The camera is preferably a video camera so that the quality of the undersurface 20 of any pin may be assessed actually during the test, or the camera may permanently record the images upon photographic film.

The prism 56 is not necessary in a modification of the embodiment (not shown) when the camera is aligned directly beneath the holes 40 and 48.

In use of the inspection device, the groups of diodes may be fired by the electric circuit either together or selectively as single groups or as combinations of groups to obtain the desired lighting upon the undersurfaces 20 of the free ends of the series of pins 18 disposed in the restricted field of view 24. Many different types of illuminated images can be reflected to the camera 58 for study purposes. Further, the diodes may be fired in a pulsed mode in which case they may collectively use a six amp current for each group.

As an example of the use of the lighting groups chosen upon the free ends of a particular series of pins, reference is made to FIGS. 5 to 7. These figures are not to scale as the component 10 together with the pins 14 are to a much larger scale than the representations of the diodes 32. The reason for this is to give a clear representation of how the light is provided in the restricted field of view.

As shown in FIG. 5, the particular series of pins 14 of the component 10 which are presently under examination, tend to extend outwardly from the body 12 from their fixed ends towards their free ends 18. Because of this, any light shone directly upon the inclined inwardly facing surfaces 60 of the pins from the diodes on the opposite side of the dish 34, i.e. generally in the direction of chain-dotted arrow 62 in FIG. 5, may cause an undesirable degree of reflection in the direction of arrow 64 through the holes 40 and 48 to the camera. This could cause confusion and difficulty in being able to determine the position of the inwardly facing peripheral edge 66 of the undersurface 20 of the free ends of the pins. This inwardly facing edge extends normal to the plane of FIG. 5 and is thus shown as a single point in FIG. 5 by a lead line 66. The inwardly facing edge 66 is shown more clearly in FIG. 7.

To prevent the above problem from arising, groups of diodes are chosen for operation which will cause a negligible or lack of reflection from the pin surfaces 60 and through the holes 40 and 48. As shown by FIG. 5, with each group of diodes lying completely at one side of dish 34 from the hole 40, the restricted field of view 24 in the region of the free ends of the pins extends laterally beyond the pairs. However, as may be seen from the theoretical edges of the converging light, shown by chain-dotted lines 68 in FIG. 5, while light is directly shone onto the whole of each under-surface 20 of the pins 14 for reflection through holes 40 and 48, no other surface of the pins will reflect light through the holes with an intensity which cause confusion to a reading of the peripheral edge region of each of the undersurfaces. The only surface which has any directional component towards the hole 40 is surface 60 and with light shining upwardly from the inner ring of diodes either at a low angle to that surface or so as to place the surface in shadow, only an extremely poor quality of illumination is able to return and pass through the hole 40.

Also, as shown in FIG. 6, the chosen groups of diodes may extend for approximately 180° around the dish between the two spaced diodes 32 and around the chain-dotted arc 70 shown therein. For 180°, in this embodiment, there are five groups of diodes which may be operated together or selectively as desired.

FIG. 7 shows the theoretical edges 68 of the light in that view to provide the restricted field of view laterally beyond a chosen series of pins with the ends of all of those pins illuminated.

As may be seen from the above embodiment, the illumination device is of simple construction and is easily operated with selected diode groups directed together upon the restricted field of view 24. Because of the use of diodes, there are little maintenance requirements as compared to a conventional inspection device. In addition, the illumination device of the embodiment and of the invention may be operated so as not to allow for light to be reflected from side surfaces of pins and which could misrepresent the true shape and position of the undersurfaces 20 of the pins so that inaccurate readings cannot be obtained. Furthermore, different types of images may be reflected from the same surface 20, dependent upon the groups of combination of groups of diodes used at any particular time, so that a true representation of the peripheral edge and position of each undersurface 20 may more accurately be obtained.

What is claimed is:

1. An illumination device for an inspection system comprising a mounting means for mounting a plurality of spaced apart light emitting diodes in mounting locations disposed in a part spherical array to cause light from the diodes to converge upon a particular restricted field of view, and a location means for locating an article to be illuminated in the restricted field of view.

2. An illumination device according to claim 1 wherein the mounting means comprises a dish with a part spherical concave surface, the dish formed with mounting apertures for holding the diodes within the wall of the dish, the apertures opening at the concave surface of the dish to direct light from the diodes at said restricted field of view which is confronted by the concave surface.

3. An illumination device according to claim 2 wherein the mounting apertures are located on coaxial pitch circles with a center of the restricted field of view coincident with the axis of the pitch circles.

4. An illumination device according to claim 2 wherein a hole for light passage is formed symmetrically through the center of the dish, the mounting apertures are located on pitch circles having centers coincident with the light passage hole, said restricted field of view being in axial alignment with the light passage hole, and there is provided a light sensitive recording means positioned to record light reflected from an article disposed in the restricted field of view and transmitted through the light passage hole.

5. An illumination device according to claim 4 including a prism aligned through the light passage hole with said specific position for redirecting light passing through the light passage hole to the light sensitive recording means.

6. An illumination device according to claim 4 wherein the light sensitive recording means comprises a camera.

7. An illumination device according to claim 1 provided with an electrical circuit having terminals at the mounting locations for the diodes at each of the mounting apertures, the terminals being electrically connected into the circuit in groups of mounting locations with the circuit operable to operate selectively a certain group or groups of diodes corresponding to the groups of terminals.

8. An illumination device according to claim 2 provided with an electrical circuit having terminals at the mounting locations for the diodes at each of the mounting apertures, the terminals electrically connected into the circuit in groups of mounting locations with the circuit operable to operate selectively a certain group or groups of diodes corresponding to the groups of terminals, and wherein the groups of mounting locations are arranged in adjacent sectors around the concave surface of the dish.

9. An illumination device according to claim 3 provided with an electrical circuit having terminals at the mounting locations for the diodes at each of the mounting apertures, the terminals being electrically connected into the circuit in groups of mounting locations with the circuit operable to operate selectively a certain group or groups of diodes corresponding to the groups of terminals and with the mounting positions of each group disposed upon a common pitch circle.

10. An illumination device according to claim 1 having infrared light emitting diodes held by the mounting means.

11. An illumination device according to claim 1 having red light emitting diodes held by the mounting means.

12. An illumination device according to claim 10 wherein a light sensitive recording means is positioned to record light patterns reflected to the recording means from an article disposed in the restricted field of view and an electrical circuit is provided to operate the infrared light emitting diodes and the operation of the infrared light emitting diodes and the recording means are synchronized whereby a light burst upon an article disposed in the restricted field of view produces a reflected light which is recorded by the recording means.

* * * * *